US00PP29656P2

(12) United States Plant Patent
Horvath

(10) Patent No.: US PP29,656 P2
(45) Date of Patent: Sep. 11, 2018

(54) ***GEUM* PLANT NAMED 'SOLID GOLD DANCER'**

(50) Latin Name: ***Geum* hybrid**
Varietal Denomination: Solid Gold Dancer

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 15/530,005

(22) Filed: Nov. 18, 2016

(51) Int. Cl.
*A01H 5/02* (2018.01)

(52) U.S. Cl.
USPC ..... Plt./263.1

(58) Field of Classification Search
USPC ..... Plt./263.1
CPC ..... A01H 5/02; A01H 5/0216; A01H 5/00
See application file for complete search history.

*Primary Examiner* — June Hwu

(57) ABSTRACT

A new, distinct *Geum* plant as shown and described, characterized by semi-double, ruffled gold petals on gold colored flowers.

1 Drawing Sheet

Latin name: *Geum* hybrid.
Cultivar name: 'Solid Gold Dancer'.

BACKGROUND OF THE INVENTION

The present invention relates to a new and distinct hybrid of *Geum* plant named 'Solid Gold Dancer' characterized by semi-double, ruffled gold flowers on up to 35 cm stems. The new *Geum* was discovered and developed as a seedling of unknown parentage as part of an on going breeding and selecting program, in Hebron, Ill. in 2014. The selection of the new plant was due to its semi-double, ruffled gold flowers. The initial asexual propagation of the new plant was by division and took place at a nursery in Hebron, Ill. since 2015. Continued asexual propagation by division since that time has shown that the unique features of this new *Geum* plant are stable and reproduced true to type in successive generations. No plants of the new *Geum* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

In the following description, color references are made to The Royal Horticultural Society Colour Chart (2001). The new *Geum* plant named 'Solid Gold Dancer' is characterized by semi-double, ruffled gold flowers of RHS 23 A. The parents of the new plant are no longer available for comparison.

The new *Geum* plant can be compared to 'Alabama Slammer' U.S. Plant Pat. No. 23,750, flower colors are orange RHS 44 A blending into red RHS 34 A while the new plant flower color is RHS 23 A. Also the size of *Geum* 'Alabama Slammer' plants are 35 cm while the new *Geum* plant reached 29 cm in maturity.

The new plant can also be compared to *Geum* 'Totally Tangerine' U.S. Plant Pat. No. 22,041, which is a sterile hybrid with lighter orange single flowers of 32 A, that fades to 169 C while the new plant color is 23 A. Plants of *Geum* 'Totally Tangerine' also grow to 130 cm tall while the new plant only grows 29 cm tall at maturity.

DESCRIPTION OF PHOTOGRAPHS

Figure 1:
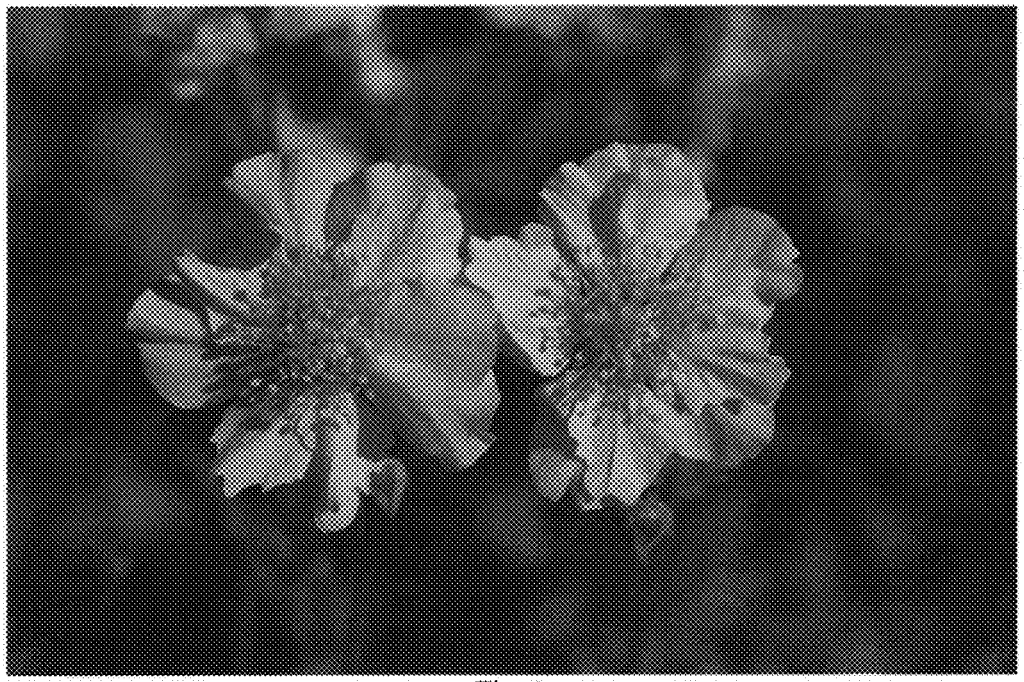
Figure 2:
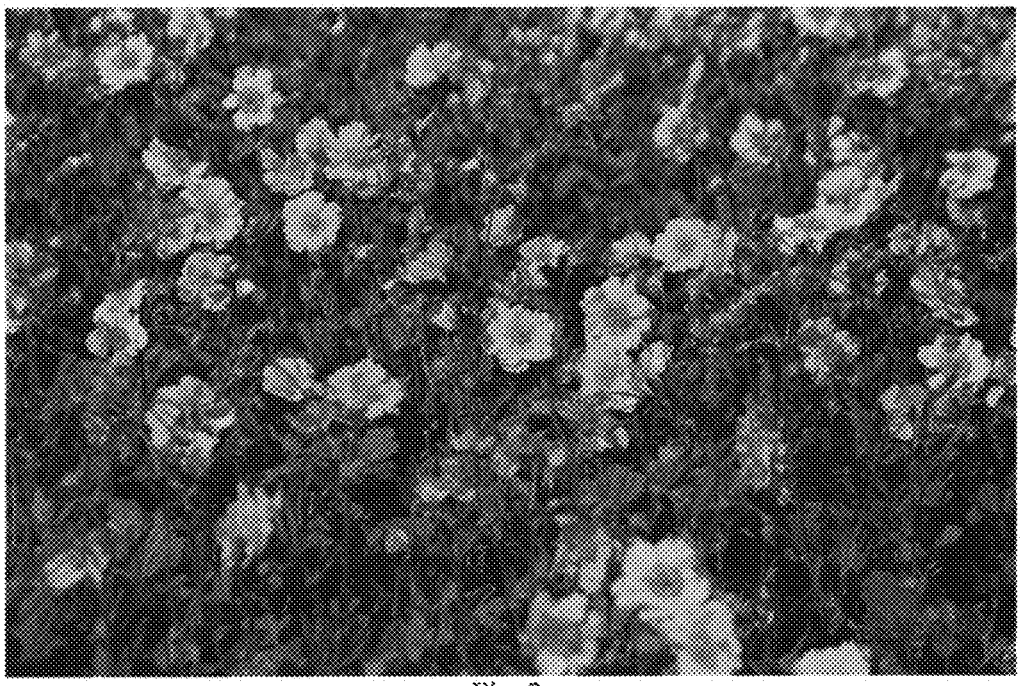

FIG. 1. Close up of the flower.
FIG. 2. Blooming plants in May.

DETAILED BOTANICAL DESCRIPTION

In the following description, color references are made to The Royal Horticultural Society Colour Chart (2001). Plants used for the description were grown in a 1 gallon container for two years at a nursery in Hebron, Ill. Measurements and numerical values represent averages of typical plants.

Botanical classification: *Geum* hybrid cultivar 'Solid Gold Dancer'.

Parentage: Seed of open pollinated plants.

Propagation: Vegetative division.

Plant description: Overall habit of the new *Geum* is basal clumps, upright green flower stems topped by semi-double gold flowers.

*Plant type*.—Herbaceous perennial.

*Plant height*.—29 cm.

*Plant width*.—44 cm.

*Stem*.—Diameter: 3 mm.

*Stem or basal branches*.—Number of basal branches per plant: 35, length up to 35 cm, with the internode between basal foliage and first leaflet length being 3 cm and the second internode between the first leaflet and the second leaflet length being 5 cm and the third internode between the second and third leaflet length being 5 cm and the fourth internode between the third and fourth leaflet length being 7 cm.

*Stem coloration*.—145 A.

Foliage description:

*Type*.—Herbaceous.

*Arrangement*.—Radical with typically three cauline leaves with lyrate shape per stem.

*Radical leaves*.—Pubescent, pinnate, upper surface color 146 A and lower surface color is 146 C.

*Petiole*.—Up to 20 cm long, with a diameter of 3 mm, color 145 A.

*Cauline terminal leaves*.—Length up to 9 cm, width — 5 cm, shape — lyrate, upper surface color 146 A and lower surface color is 146 C.

*Cauline lateral leaves*.—Length — typically 4 cm, width — typically 2 cm, shape — lyrate, apex: Acute, leaf base — Cuneate, margin — incised, upper surface color 146 A and lower surface color is 146 C.

*Texture*.—Cauline leaves, upper and lower surfaces: pubescent.

*Venation pattern*.—Cauline leaves, upper and lower surfaces: lyrate.

*Venation color*.—Cauline leaves, upper surface is color 146 A and lower surface color is 146 C.

*Cauline leaves number*.—3 per stem.

*Cauline leaves length*.—6 cm.

*Cauline leaves width*.—Up to 5 cm.

*Cauline leaves shape*.—Lyrate.

*Adaxial leaf description*.—Color is 146 A. Abaxial Leaf Description — color 146 C.

Flower description:

*Flower type*.—Corymb.

*Flower color*.—23 A fading to 23 B on top and 13 A fading to 16 A on the bottom.

*Flower size*.—Diameter: 40 mm across, depth 18 mm.

*Flower number*.—5 per stem, 125 per plant.

*Number flowering stems*.—25.

*Bloom period and duration*.—Beginning the first week of May into the first week of June in Hebron, Ill.

*Flower longevity and duration on the plant*.—Approximately 3 weeks.

*Flower longevity and duration cut*.—Approximately one week.

*Individual flower duration*.—Approximately 1 to 2 weeks with petals eventually drying to a tan color.

*Scent*.—None.

*Petal count*.—13.

*Petal shape*.—Spatulate.

*Petal arrangement*.—Both lobulated and rotate, overlapping.

*Petal diameter or width*.—16 mm across and petal length — 16 mm long.

*Petal apex*.—Reuse, base: attenuate, margin: both sinuate and entire.

*Petal texture*.—Upper and lower surfaces: smooth, glabrous.

*Petal color*.—Upper surface is color 23 A fading to 23 B.

*Petal color*.—Lower surface color is close to 13 A fading to 16 A.

*Overall corymb size*.—Diameter and height — 11 cm across, 13 cm long.

*Flower buds*.—Diameter: 10 mm across, depth: 15 mm, shape: ovoid, surface: slightly pubescent and color 59 B.

*Sepal size*.—Length: up to 12 mm, diameter: 7 mm at base coming to a point.

*Sepal quantity*.—5.

*Sepal shape*.—Lanceolate, apex: acute, base: cuneate, margin: entire.

*Sepal texture*.—Upper and lower surfaces: Pubescent.

*Sepal color*.—Adaxial color is 146 D. Abaxial color 146 C.

*Peduncle color*.—145 A.

*Peduncle size*.—Length: 26 mm, diameter: 3 mm.

*Pedicel size*.—Length: 30 mm, diameter: 1-2 mm and typically color 145 A, sometimes taking on a slight reddish color.

*Reproductive organs*.—Stamen — average quantity 150, length 8 mm.

*Anther*.—Average quantity: 150, length: 1 mm, diameter: close to 1 mm.

*Pollen*.—Typically present, color: 23 A.

*Stigma*.—Average number 65, Length: 6 mm, width less than 1 mm, general color is orange.

*Style*.—Average number: 65, length: 8 mm, general color is orange. Green at base 146 D, orange at tip 23 B.

*Pistil*.—Average number: 65, length: 4 mm.

*Ovaries*.—Average number: 65 per bloom average, color: is green 146 D.

*Fruit*.—Average number: 65 per bloom average, Size is typically small to medium, color: is brown, type: cluster of achenes with long styles tear shaped, length — 9-10 mm, width — 2 mm.

*Hardiness*.—USDA zone 4 to 9.

Disease resistance: Resistance to diseases common to *Geum* has not been observed on plants grown under nursery conditions.

I claim:

1. A new, distinct *Geum* plant as illustrated and described, characterized by semi-double, ruffled gold petals on gold colored flowers.

* * * * *